United States Patent [19]

Murray et al.

[11] Patent Number: 5,234,677
[45] Date of Patent: Aug. 10, 1993

[54] ENHANCED EFFICACY ALUMINUM CHLORHYDRATE ANTIPERSPIRANT AND METHOD OF MAKING SAME

[75] Inventors: Robert W. Murray, Lebanon, N.J.; Roger E. Nelson, Hatfield, Pa.; Andrew M. Rubino, New Providence, N.J.

[73] Assignee: Reheis Inc., Berkeley Heights, N.J.

[21] Appl. No.: 547,402

[22] Filed: Jul. 2, 1990

Related U.S. Application Data

[63] Continuation of Ser. No. 102,296, Sep. 25, 1987, abandoned, which is a continuation of Ser. No. 673,959, Nov. 21, 1984, abandoned.

[51] Int. Cl.$^5$ .................... A61K 7/38; C01F 7/56
[52] U.S. Cl. ........................... 423/462; 424/68
[58] Field of Search ........................... 424/68; 423/462

[56] References Cited

U.S. PATENT DOCUMENTS

| 3,904,741 | 9/1975 | Jones et al. ............... 423/462 |
| 4,359,456 | 11/1982 | Gosling et al. ............ 423/462 |

FOREIGN PATENT DOCUMENTS

| 0006739 | 1/1980 | European Pat. Off. |
| 41600 | 11/1976 | Japan ........................ 423/462 |
| 1335631 | 10/1973 | United Kingdom. |
| 1568831 | 6/1980 | United Kingdom. |
| 2048229 | 12/1980 | United Kingdom ........... 423/462 |

OTHER PUBLICATIONS

R. Buman et al., *Latvijas Psr Zinatsu Akademijas Vetis, Kimijas Serija*, No. 4, (1973) 421–426.
Chlorhydrol® 50% w/w Solution Reheis Technical Data, Reheis Chemical Company.

*Primary Examiner*—Jeffrey E. Russel
*Attorney, Agent, or Firm*—Panitch Schwarze Jacobs and Nadel

[57] ABSTRACT

Two-thirds to five-sixths basic aluminum chlorides having enhanced antiperspirant efficacy are produced by heating an aqueous solution containing about 40 to about 50 weight percent of the basic aluminum chloride to a temperature of at least about 130 degrees C. for about one to twelve hours in a closed vessel, with the heating time being inversely proportional to the temperature. Five-sixths basic aluminum chlorides treated in this manner are characterized by a size exclusion chromatogram having a single major peak with its apex at a relative retention time of about 0.75–0.79. The basic aluminum chlorides may be incorporated into any of the conventional antiperspirant forms with non-toxic, dermatologically acceptable carriers.

10 Claims, 1 Drawing Sheet

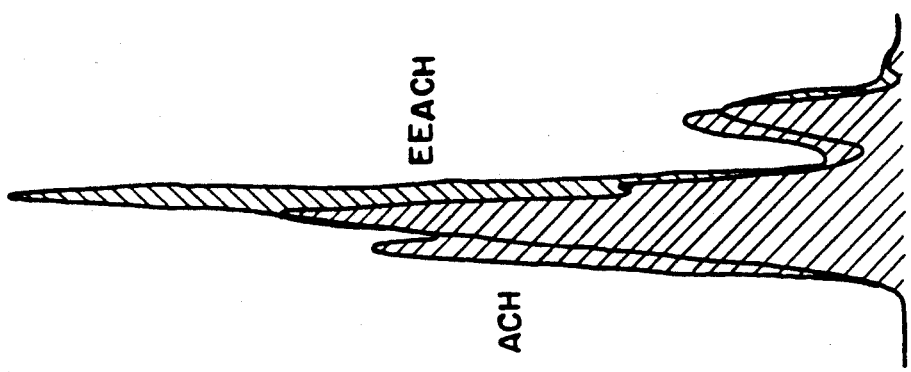
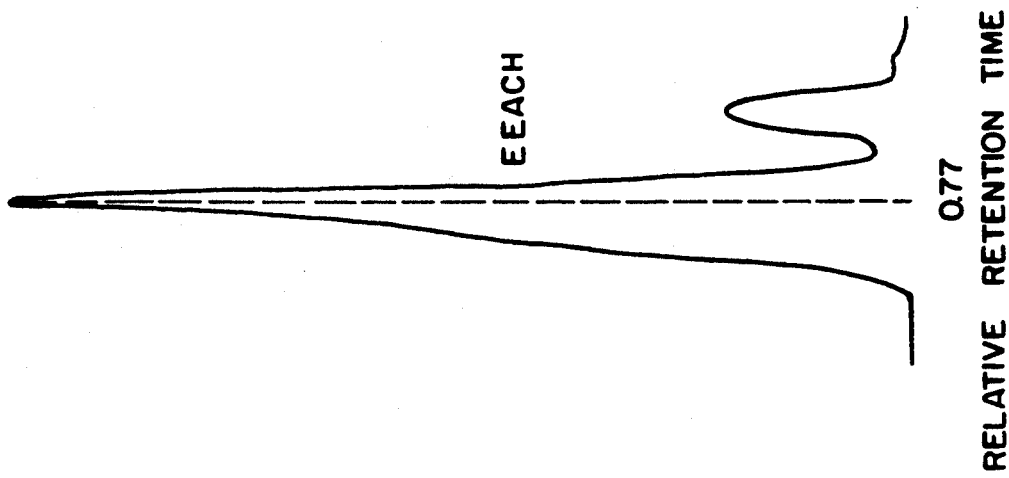
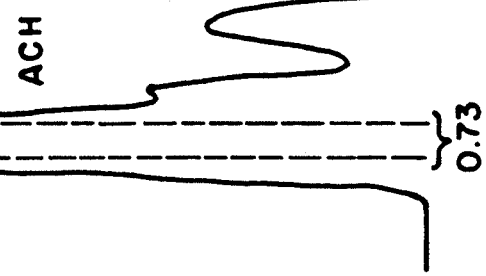

ENHANCED EFFICACY ALUMINUM CHLORHYDRATE ANTIPERSPIRANT AND METHOD OF MAKING SAME

CROSS REFERENCE TO RELATED APPLICATIONS

This application is a continuation of our copending application Ser. No. 102,296, filed Sep. 25, 1987, which in turn was a continuation of application Ser. No. 673,959, filed Nov. 21, 1984, both now abandoned.

FIELD OF THE INVENTION

The present invention relates to the production of aluminum chlorhydrates having enhanced antiperspirant efficacy. More particularly, the invention relates to the heat treatment of basic aluminum chlorides to improve their antiperspirant activity.

BACKGROUND OF THE INVENTION

Aluminum chlorhydrates (also referred to as aluminum chlorhydroxides or basic aluminum chlorides) have been known and used for many years as effective antiperspirants, and still constitute the essential active ingredient in many antiperspirants today. The aluminum chlorhydroxides are complex structures made up of mixtures of polymeric and monomeric species of various sizes and molecular structures, together with varying amounts of bound or coordinated water. They are generally represented by the empirical formula:

$$Al_2(OH)_{(6-x)}Cl_x$$

wherein $0 < x < 6$ and need not be an integer. It should be understood that the above formula is greatly simplified and is intended to include basic aluminum chlorides containing coordinated or bound molecules of water as well as basic aluminum chloride polymers, complexes and mixtures of the above.

Particularly preferred aluminum chlorhydrates are those in which x is in the range of about 1 to 2, and preferably about 1, the latter being referred to as five-sixths basic aluminum chloride. Such compounds have a predominance of units of the above formula in which x is between about 1 and 2, such that the aluminum to chlorine mole (Al/Cl) ratio is on the order of about 1/1 to 2.1/1, and usually in the range of about 1.9/1 to 2.1/1.

For many years five-sixths basic aluminum chloride has been recognized as the standard active ingredient for antiperspirants. It has been available in various forms, typically in 50 weight percent aqueous solution (commercially available from Reheis Chemical Company under the trademark "CHLORHYDROL"), but also in various dry forms obtained by spray drying aqueous solutions to an extent which does not remove all of the bound or coordinated water. In addition, these compounds may be co-dried or otherwise combined with any of a number of adjuvants and/or additives designed to perform various functions, such as buffers; these could include such moieties as glycine, urea, polyols, etc.

In the past twenty years many attempts have been made to improve the antiperspirant efficacy and other properties of the basic aluminum chlorides, some by the formation of complexes with various organic and inorganic additives to the basic aluminum chloride complexes. Among the attempts to modify the complex structure of the basic aluminum chlorides without the addition of other entities, three are noteworthy in relation to the present invention.

U.S. Pat. No. 3,904,741 of Jones et al (assigned to the same assignee as the present invention) discloses two-thirds to five-sixths basic aluminum chloride solids which have been rendered alcohol soluble by heating a solution of basic aluminum chloride under reflux conditions, preferably to a temperature of about 100 degrees C. for about two to four hours, and then drying the refluxed solution, preferably by spray drying, to a carefully controlled content of free and coordinated water. The patentees theorized that the refluxing promoted a shift in the species of basic aluminum chloride molecules from higher molecular weight to lower molecular weight species.

More recently, published British patent application No. 2,048,229 of Fitzgerald et al (assigned to the Gillette Company) disclosed a modification of aluminum chlorhydroxide, preferably five-sixths basic aluminum chlorhydroxide, by aging a 5 to 40 weight percent solution (most preferably a 10 to 25 weight percent solution) at a temperature between 50 and 100 degrees C. for a period of at least eight hours up to a week or more. The type of aging vessel is not stated, but it is apparently an open, non-pressurized vessel with compensation being made for loss of water during heating; otherwise a dried solid could result. After aging the solution can be concentrated by distillation and then spray dried. According to this patent application the aging process modifies the aluminum chlorhydroxide by increasing the amount of the more efficacious group of $Al^{c'}$ complexes (as defined in the British application) from about 10 to 30 weight percent in conventional aluminum chlorhydroxides to a level of at least 45 weight percent and preferably more than 60 or 70 weight percent in the aged aluminum chlorhydroxides. These higher percentages of $Al^{c'}$ complexes are broadly characterized by their diffusion constants in gel permeation chromatography.

Another recent modification of basic aluminum compounds is disclosed in U.S. Pat. No. 4,359,456 of Gosling et al (assigned to Lever Brothers Company). According to the method of that patent, a wide range of basic aluminum chlorides in a 10 to 34 weight percent aqueous solution (2.5–8.5 weight percent aluminum) is heated to a temperature of 50 to 140 degrees C. for a period of time sufficient to cause the basic aluminum compound to have a Size Exclusion Chromatography Test Band having a relative retention time corresponding to Band III of the standard basic aluminum chloride solution Size Exclusion Chromatogram and a Band III Aluminum Value of at least 20 percent. The heating is carried out for a period of from one-half hour to 30 days in a closed tube, bottle or reactor, followed by cooling to ambient temperature and drying to a water soluble powder. The increase of the percentage of aluminum in the Band III fraction to a level of 20 percent or more is said to result in an enhancement of the antiperspirant activity of the basic aluminum chloride. In contrast, according to that patent, 40 or 50 weight percent solutions of approximately five-sixths basic aluminum chloride heated to 120 degrees C. for 24 hours in glass screw-cap tubes did not result in enhanced antiperspirant activity or Band III levels of aluminum greater than 20 percent by weight.

BRIEF SUMMARY OF THE INVENTION

According to the present invention the antiperspirant activity of approximately two-thirds to five-sixths basic aluminum chlorides may be enhanced by heating an aqueous solution containing about 40 to about 50 weight percent of the basic aluminum chloride to a temperature of at least about 130 degrees C. for about one to twelve hours, with the heating time being inversely proportional to the temperature, in a closed vessel, followed by cooling of the solution, and optionally drying the solution to a solid, such as by spray drying.

Preferred approximately five-sixths basic aluminum chlorides of the invention have a gel permeation chromatogram (GPC) characterized by a single major peak with its apex at a relative retention time of about 0.75 to 0.79, and preferably about 0.77. Preferably, the area under the peak represents at least 60 percent, and preferably at least 75 percent, of the total area under the chromatogram.

Particularly preferred basic aluminum chlorides according to the invention are produced by heating an approximately 50 weight percent solution of five-sixths basic aluminum chloride having an Al/Cl ratio of about 1.9/1 to 2.1/1 to a temperature of about 140 degrees C. for about 7 to 8 hours, followed by cooling and spray drying the solution. The resulting product when incorporated into conventional antiperspirant formulations has enhanced antiperspirant efficacy compared to unmodified five-sixths basic aluminum chloride formulations having the same weight percent of active ingredient.

The enhanced efficacy basic aluminum chlorides of the present invention may be made into antiperspirant compositions with virtually any of the usual vehicles and formulations known in the art.

BRIEF DESCRIPTION OF DRAWING

FIG. 1A is a typical size exclusion chromatogram of a sample of an untreated 50 weight percent (solids) solution of aluminum chlorhydrate (ACH), using the GPC procedure described below.

FIG. 1B is a typical size exclusion chromatogram of a sample of enhanced efficacy aluminum chlorhydrate (EEACH) made according to the present invention, using the same GPC procedure as for FIG. 1A.

FIG. 1C is a composite of FIGS. 1A and 1B more clearly illustrating the shift of peaks (representing changes in basic aluminum chloride species) resulting from the method of the present invention.

DETAILED DESCRIPTION OF THE PREFERRED EMBODIMENTS

As indicated above, an aqueous solution containing 50 percent by weight of five-sixths basic aluminum chloride (approximately 12.5 weight percent aluminum) is commercially available from Reheis Chemical Company under the trademark "CHLORHYDROL". Alternatively, the aqueous solution of basic aluminum chloride may be made directly (e.g., by the conventional reaction of aluminum metal with $AlCl_3$ or HCl in water solution) to the desired range of Al/Cl ratio. The Al/Cl ratio may be adjusted to the desired range by adding aluminum chloride ($AlCl_3$) or HCl to a commercially available or other prepared solution of basic aluminum chloride.

While it is preferred from the standpoint of production convenience to start with an aqueous solution containing 50 percent (solids) basic aluminum chloride, concentrations of about 40 to about 50 weight percent basic aluminum chloride may be used in the present invention. Such solutions may be prepared by adjusting the concentration of a commercially available "CHLORHYDROL" solution or by making the basic aluminum chloride solution directly to the desired concentration.

Similarly, while a five-sixths basic aluminum chloride having an Al/Cl ratio of approximately 2/1 is preferred due to its commercial availability and recognized efficacy, basic aluminum chlorides having Al/Cl ratios of about 1/1 to 2.1/1 may be used in the present invention, and will be understood to fall within the term "approximately two-thirds to five-sixths basic aluminum chlorides".

The heating of the aqueous solution to obtain basic aluminum chloride species with enhanced antiperspirant efficacy according to the present invention may be carried out in any suitable vessel which may be closed so that the system is pressurized to the vapor pressure of the solution at the temperature to which heating is desired (e.g. about 40 psig at 140 degrees C.). For example, the heating may be carried out in screw-cap pressure tubes which are placed in a fan oven for the heating or in a bomb type stirred reactor with its own electric heating elements. Other suitable reactors will be obvious to those skilled in the art.

The aqueous solution of basic aluminum chloride is heated to a temperature of at least about 130 degrees C., preferably between about 130 and 160 degrees C. and optimally from about 140 to 150 degrees C., for a period of about one to about twelve hours, with the heating time being inversely proportional to the temperature. That is, whereas heating temperatures of about 130 degrees C. may require a heating time of as much as ten to twelve hours or more, heating temperatures above about 160 degrees C. may only require an hour or less. Heating for times longer than required for complete conversion at any given temperature may result in the formation of excessive amounts of insolubles or gels. Also, it will be understood that a certain amount of conversion may occur during the periods of heating up to the final temperature or cooling down, so that indicated "on temperature" periods may be somewhat shorter depending on the particular heating apparatus and speed of bringing up to temperature or cooling down.

Optimum reaction conditions for forming the enhanced efficacy products of the present invention appear to be heating at about 140 degrees C. for about 7 to 8 hours in the case of a 50 weight percent basic aluminum chloride solution. In general, it has been found that each 5 degree C. temperature increase shortens the reaction time by about 1 to 1½ hours. Thus, laboratory experiments indicate that conversion of the basic aluminum chloride solutions to the more active basic aluminum chloride antiperspirant species of the present invention is complete in about 1.5-2 hours at a reaction temperature of about 160 degrees C., in about 5 hours at about 150 degrees C., in about 6 hours at about 145 degrees C. and in about 7 hours at about 140 degrees C.

The appropriate end point of the heating of the solution, which should correspond substantially with the completion of the conversion of the two-thirds to five-sixths basic aluminum chloride to the enhanced activity entities of the present invention, may be determined by measuring various physical or chemical properties of the basic aluminum chloride. One such determination involves the use of gel permeation chromatography (GPC) sometimes referred to as size exclusion chromatography, in a manner similar to that described in the above mentioned U.S. Pat. No. 4,359,456 of Lever Brothers Company to determine the separation of various aluminum-containing fractions and their relative retention times in the chromatography column. For these determinations, a Waters HPLC instrument was used with a U6K LC injector, a 6000 A solvent delivery system, a R401 differential refractometer and a 730 data module. The chromatographic column was an E. Merck "Lichrosorb RP-2" silica column. The column was 25 cm long with an ID of 4.6 mm, a pore size of 60 Angstroms and a particle size of 5 microns.

Basic aluminum chloride samples were dissolved in deionized water at a concentration of 2.5 percent aluminum, filtered if necessary and were chromatographed promptly. Samples of 3 microliters were used at a flow rate of 0.2 ml per minute, a chart speed of 0.5 cm per minute, and 0.01N $HNO_3$ eluent.

Using the above equipment and procedure, it has been found in the case of approximately five-sixths basic aluminum chlorides that the heating according to the present invention causes a shift in the aluminum containing species from two major fractions for the untreated 50 percent basic aluminum chloride solution to one major fraction with a longer average retention time for the enhanced activity products of the present invention. This shift of species is illustrated in the accompanying drawings.

As illustrated in FIG. 1A, a typical size exclusion chromatogram produced according to the above procedure on samples of 50 weight percent "CHLORHYDROL" solutions showed two major peaks which represent the two major fractions of aluminum containing species corresponding to those described as Band I and Band II in U.S. Pat. No. 4,359,456 discussed above. As in that patent, the fractions are characterized by means of the ratio of their respective retention times in the column to retention time of the totally included species from the eluted basic aluminum chloride sample. The average relative retention time for the two major fractions in a 50 percent "CHLORHYDROL" solution (taken as the straight average of the relative retention times of the apices of the two peaks) is about 0.73, with a range of about 0.70-0.77 for a series of plant batches tested. In contrast as shown in FIG. 1B, a series of production plant batches made generally according to the method of Example III below showed one major peak with an average relative retention time of the apex of 0.77, with a range of 0.75-0.79 for the samples tested. FIG. 1C illustrates this shift more clearly by superimposing the chromatograms of FIGS. 1A and 1B. The shading in FIG. 1C represents the area of overlap of the chromatograms of FIGS. 1A and 1B.

It will be understood by those of ordinary skill in the art that the relative retention times of various fractions will vary slightly due to a number of factors including the particular column and procedure used, the age of the column and the peak which is taken as the last one for calculation of the relative time for the other peaks on the chromatograph.

After the heating has been completed, the solution is preferably cooled and optionally filtered to remove insoluble particles. The cooling and filtration steps are not critical and appropriate methods and means for carrying out these steps will be apparent to those of ordinary skill in the art. In general, the cooling is only necessary to a degree to complete the conversion reaction and stop formation of insolubles and to allow for further desired processing. Filtration is required only where it is considered desirable to remove insolubles.

Although the enhanced activity basic aluminum chlorides of the present invention may be used in any of the conventional forms of antiperspirant formulations, including inter alia a diluted aqueous solution, it is generally preferred to dry the basic aluminum chloride solution to a solid for purposes of shipping, storing and further handling. It is particularly preferred that the solution be dried in a spray dryer. If the filtration step is omitted, the cooling step may also be omitted or modified so that the solution temperature is simply adjusted to the appropriate inlet temperature for the spray dryer, where the product is to be spray dried to a solid.

Spray drying is well known to those in the antiperspirant art, and the particular spray drying conditions will depend upon such factors as the desired particle size, desired degree of dryness and particle form.

Of course, it will be evident to those of ordinary skill in the art that other means of drying such as ambient tray drying, oven drying, vacuum or freeze-drying may be used to form the final product, and the method of drying is not critical to the invention, so long as the solution is not over dried to form excessive amounts of insoluble particles or to degrade the antiperspirant activity of the basic aluminum chloride. After drying, the solid particles may be screened, sifted, ground or otherwise classified to form powders of the desired particle size range.

The resulting basic aluminum chloride solids of the invention may be incorporated into various conventional antiperspirant forms such as solutions (aqueous, non-aqueous or alcoholic), aerosols, powders, sticks, lotions, roll-ons, gels, creams and the like, which may contain a variety of non-toxic, dermatologically acceptable moieties such as solvents, emollients, propellants, perfumes, etc. The basic aluminum chlorides of the invention retain the excellent water solubility of the untreated basic aluminum chloride, and also have a certain amount of alcohol solubility, particularly if the content of free and coordinated water is carefully controlled, similarly to the method of U.S. Pat. No. 3,904,741.

The invention will now be described in more detail with reference to the following specific, non-limiting examples:

EXAMPLE I 1200 grams of a 50% "CHLORHYDROL" solution was charged to a 2 liter bench model No. 4522 Parr stirred reactor with temperature controller. The solution was stirred at a slow rate and heated to a pressure of 40 psig (140 degrees C.) over a period of one hour. The solution was then held on temperature for seven hours, followed by cooling to a temperature of 90 degrees C. over a period of 45 minutes, at which point the reactor was vented to the atmosphere and opened. The contents of the reactor were removed and insolubles were filtered out by suction filtration.

A sample of the cooled solution was diluted to a concentration of 10 weight percent solids, and a chromatograph was run using the GPC procedure described above. The chromatogram showed a single major peak with its apex at a relative retention time of 0.76, and the area of the major peak represented 82.7% of the total area.

EXAMPLE II 100 ml of 50% "CHLORHYDROL" solution was placed in a Wheaton 400 pressure bottle with a 200 ml capacity. The top was clamped shut, and the bottle was placed in a Blue M Electric Co. forced draft oven heated to 160 degrees C. It took approximately one hour for the bottle and contents to reach the 160 degrees C. temperature, and the solution was held on temperature for two hours, after which it was removed from the oven and allowed to cool in a hood before opening.

A chromatograph was run as in Example I; the chromatogram showed a single major peak with the apex of the peak at a relative retention time of 0.75; and 83.1 percent of the total area was represented within the peak.

EXAMPLE III

In a plant production run 22,000 pounds of 50% "CHLORHYDROL" solution was charged to a 2000 gallon glass lined reactor which was sealed and heated over a five hour period with moderate stirring to 145 degrees C. (45 psig). The solution was held on temperature for 6 hours and then cooled by a water jacket over a three hour period to about 40-50 degrees C. The solution was then filtered warm through a large plate and frame filter press to remove insolubles. The filtered solution was dried in a spray dryer to a powder.

A sample of the powder made up to a 10 percent aqueous solution was chromatographed as in Example I above. The chromatogram showed a single major peak with its apex at a relative retention time of 0.78, and 79.5 percent of the total area was represented within the peak.

To evaluate the antiperspirant effectiveness of the enhanced efficacy aluminum chlorhydrates (EEACH) of the present invention as compared to the conventional aluminum chlorhydrate (ACH) standard of the prior art, antiperspirant efficacy tests were performed by an independent concern on the following samples:

Samples A through F were aerosol formulations containing the indicated weight percents of active ingredient (ACH or EEACH) with 75 weight percent propellant (80% isobutane/20% propane), 0.8 weight percent SDA-40, 0.8 weight percent Bentone 38, and the balance isopropyl myristate. Samples G and H were aqueous solutions prepared by diluting or dissolving the active ingredient with deionized water. The active ingredients were prepared as follows:

Sample A was a microfine powder obtained by spray drying a 50 weight percent "CHLORHYDROL" solution;

Samples B, C, D and H were prepared in a production batch as in Example III above, except that the solution was held on temperature for 8 hours at 140 degrees C.;

Sample E was prepared in the same manner as Samples B, C, D and H, except that the solution was not filtered before spray drying;

Sample F was prepared in a pilot plant reactor similar to the procedure described in Example III, except that the solution was held at a temperature of 140 degrees C. for 5 hours; and Sample G was a 50 weight percent solids "CHLORHYDROL" solution diluted with deionized water to 15 weight percent solids.

The tests were performed by axillary application to 89 female panelists in Test No. 1 and 162 female panelists in Test No. 2, who were required to abstain from use of antiperspirant materials during the study and for a period prior thereto. Sample applications were made to cover an approximately 4 by 6 inch area of one axilla of each panelist, with the opposite axilla serving as the untreated control. In the case of solution samples the application consisted of 0.5 cc of the solution applied by means of cotton swabs previously saturated in the solution, while aerosol samples were applied using a two second spray (in Test No. 1) or a 2.5 second spray (in Test No. 2), ascertained by a precalibrated metronome, from a distance of about six inches.

Sweating was induced by having the panelists sit in a room maintained at about 100 degrees F. at a relative humidity of about 35 percent. Sweat collections were made by holding weighed Webril pads against the axilla.

The sample applications and sweat collections were made according to the following schedule during each week: As a control, no sample applications were made on the first day and sweat collections were made to establish a base line. On the second day the first sample applications were made. On the third and fourth days second and third applications were made followed in an hour by sweat collection. A fourth application was made on the fourth day followed by a one hour wait and then sweat collection on the fifth day (22 hours following the fourth application).

In all cases sweating ratios were calculated by dividing the amount of sweat collected from the test axilla by that obtained from the control axilla and mean percentage sweat reduction rates were calculated. The percent reductions

TABLE I

| | Appln. #2 (1 Hr.) | | Appln. #3 (1 Hr.) | | Appln. #4 (22 Hrs.) | | Significance Levels (%) v. ACH (Appln. #4-22 hrs) | | |
|---|---|---|---|---|---|---|---|---|---|
| | #1 | #2 | #1 | #2 | #1 | #2 | #1 | #2 | Test comb. |
| AEROSOLS | | | | | | | | | |
| A - 10% ACH | 24.5 | 33.9 | 24.1 | 34.4 | 29.9 | 40.5 | | | |
| B - 5% EEACH | | 28.6 | | 33.7 | | 44.3 | | <50 | |
| C - 10% EEACH | 34.8 | 41.6 | 36.8 | 45.3 | 45.1 | 53.1 | 95.2 | 93.6 | >99 |
| D - 13% EEACH | | 34.8 | | 41.9 | | 49.9 | | 84 | |
| E - 10% EEACH (Unfiltered) | | 39.0 | | 43.9 | | 55.2 | | 97.5 | |
| F - 10% EEACH (5 Hours) | | 28.7 | | 39.9 | | 51.4 | | 79 | |
| SOLUTIONS | | | | | | | | | |
| G - 15% ACH | 36.6 | 46.3 | 48.3 | 47.0 | 53.7 | 52.4 | | | |

TABLE I-continued

| | ANTIPERSPIRANT EFFICACY TESTS | | | | | | | | |
|---|---|---|---|---|---|---|---|---|---|
| | Appln. #2 (1 Hr.) | | Appln. #3 (1 Hr.) | | Appln. #4 (22 Hrs.) | | Significance Levels (%) v. ACH (Appln. #4–22 hrs) | | |
| | TESTS | | | | | | | | |
| | #1 | #2 | #1 | #2 | #1 | #2 | #1 | #2 | Test comb. |
| H - 15% EEACH | 54.3 | | 56.4 | | 61.7 | | 82 | | |

The present reductions in sweating observed after the second, third and fourth applications of the test materials are shown in Table I. The 95 percent confidence limits of these values are omitted, but range from about 6 to 15 percent. The significance levels of differences between products (based on the fourth application) were calculated using the least significance difference test. Samples B through F were compared to Sample A and Sample H was compared to Sample G. The validity of the test for Sample D is questionable due to a formulation problem experienced with this sample.

From these tests it may be concluded that the enhanced efficacy basic aluminum chloride compounds of the present invention are about 30 to 50 percent more efficacious than the conventional basic aluminum chloride standard in a hydrocarbon aerosol formulation. The 10 percent aerosol formulation of the present invention is approximately equal in efficacy to a 15 percent aqueous solution of the standard basic aluminum chloride. A 15 weight percent solution of the present invention is more efficacious than a standard 15 percent solution of the basic aluminum chloride.

It will be recognized by those skilled in the art that changes may be made to the above-described embodiments of the invention without departing from the broad inventive concepts thereof. It is understood, therefore, that this invention is not limited to the particular embodiments disclosed, but it is intended to cover all modifications which are within the scope and spirit of the invention as defined by the appended claims.

We claim:

1. A method of enhancing the antiperspirant efficacy of an approximately two-thirds to five-sixths basic aluminum chloride comprising providing an aqueous solution containing about 40 to 50 weight percent of approximately two-thirds to five-sixths basic aluminum chloride, heating said solution to a temperature of at least about 130 degrees C. for about one to twelve hours, with the heating time being inversely proportional to the temperature, in a closed vessel, and cooling the resulting product.

2. A method according to claim 1 wherein said product is dried to a solid by spray drying.

3. A method according to claim 1 wherein said solution contains about 50 weight percent basic aluminum chloride.

4. A method according to claim 1 wherein said basic aluminum chloride has an Al/Cl ratio of about 1/1 to 2.1/1.

5. A method according to claim 1 wherein said solution is heated to a temperature of about 140 degrees C. for about 7 to 8 hours.

6. A method according to claim 1 wherein an approximately 50 weight percent solution of basic aluminum chloride having an Al/Cl ratio of about 1.9/1 to 2.1/1 is heated to about 140 degrees C. for about 7 to 8 hours.

7. A method according to claim 6 wherein the resulting product is spray dried.

8. A method according to claim 1 wherein said solution is heated to a temperature of about 130 to 160 degrees C.

9. A method according to claim 1 wherein said solution is heated to a temperature of about 140 to 150 degrees C.

10. A method according to claim 9 wherein said solution is heated for about 5 to 8 hours.

* * * * *